United States Patent [19]
Boström

[11] Patent Number: 5,722,425
[45] Date of Patent: Mar. 3, 1998

[54] STYLET UNIT

[75] Inventor: Mats Boström, Sundbyberg, Sweden

[73] Assignee: Pacesetter AB, Solna, Sweden

[21] Appl. No.: 758,517

[22] Filed: Nov. 29, 1996

[30] Foreign Application Priority Data

Dec. 4, 1995 [SE] Sweden ................................. 9504333

[51] Int. Cl.$^6$ .......................................................... A61B 5/00
[52] U.S. Cl. ........................... 128/772; 128/657; 128/658
[58] Field of Search ..................................... 128/772, 658, 128/657; 604/280, 281, 282, 283; 606/78

[56] References Cited

U.S. PATENT DOCUMENTS

| | | |
|---|---|---|
| 4,136,703 | 1/1979 | Wittkampf . |
| 4,170,990 | 10/1979 | Baumgart et al. ............... 606/78 |
| 4,913,147 | 4/1990 | Fahlstrom et al. . |
| 5,170,787 | 12/1992 | Lindegren . |
| 5,190,546 | 3/1993 | Jervis . |
| 5,383,923 | 1/1995 | Webster, Jr. . |
| 5,447,512 | 9/1995 | Wilson et al. ............... 604/281 |
| 5,582,609 | 12/1996 | Swanson et al. ............... 128/642 |

FOREIGN PATENT DOCUMENTS

| | | |
|---|---|---|
| 0 381 819 | 8/1990 | European Pat. Off. . |
| WO 90/13329 | 11/1990 | WIPO . |
| WO 95/13111 | 5/1995 | WIPO . |

*Primary Examiner*—Max Hindenburg
*Assistant Examiner*—Pamela Wingood
*Attorney, Agent, or Firm*—Hill, Steadman & Simpson

[57] ABSTRACT

A stylet unit, which can be introduced into a hollow, flexible component, such as an electrode cable, to stiffen the component and to bend a distal end section is formed by a double stylet combination of a flexible tubular stylet shell and an internal stylet, movably arranged inside the shell's channel, with a pre-curved distal end section. This end section can be set at a retracted internal position inside the stylet shell or at an exposed position outside the shell. The internal stylet's pre-curved distal end section is made of a memory metal and has a radius of curvature which varies longitudinally along the end section. The end section can be in the shape of a spiral, and the memory metal can be made of a nickel-titanium alloy.

7 Claims, 2 Drawing Sheets

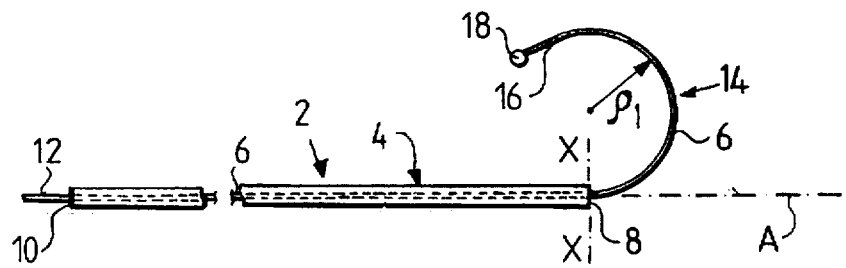
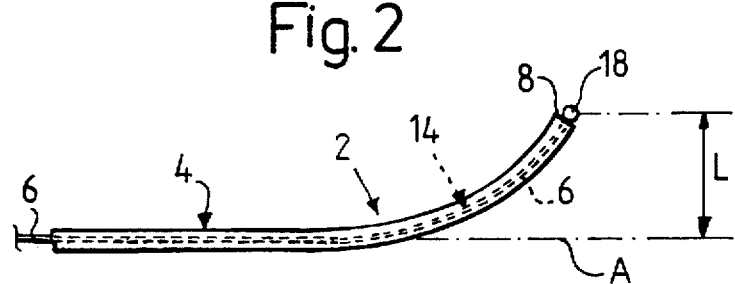
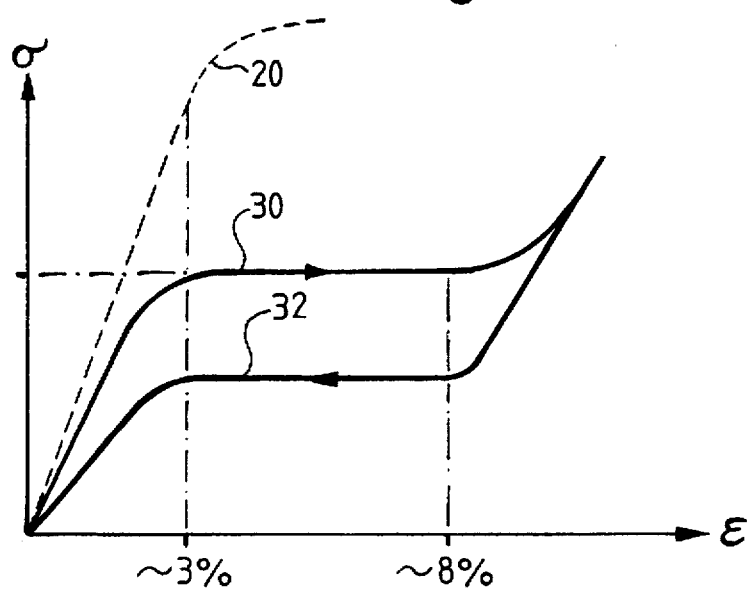

STYLET UNIT

BACKGROUND OF THE INVENTION

1. Field of the Invention

The present invention relates to a stylet unit which can be introduced into a flexible component, such as an electrode cable, catheter or some other tubular instrument, with a narrow, longitudinal, internal channel to stiffen the flexible component and to bend a distal end section of the component. More particularly, the invention relates to a stylet unit of the type formed by a double stylet combination including a flexible, tubular stylet shell and an internal stylet, movably arranged inside the shell's channel, with a pre-curved distal end section which can be set to a retracted position inside the shell or to a position projecting outside the shell.

A channeled component of the aforementioned kind could e.g. be a tubular conductor used for stimulation in the human body. Such a channeled component could be devised to serve either as an implant or for removal from the body after a medical treatment has been performed.

2. Description of the Prior Art

A stylet unit of the above general type is especially suitable for stiffening and guiding a hollow electrode cable for a heart stimulator during advancement of the electrode cable into a human heart and for anchoring a contact electrode (electrode head) on the distal end of the cable in a cavity of the heart. The introduction of such an electrode cable into the heart usually occurs through a suitable vein, and the contact electrode can be anchored either in the right ventricle or atrium. The temporarily introduced styler unit inside the hollow electrode cable extends through the cable's central channel from the cable's proximal end (which is subsequently connected to the heart stimulator) to its distal end at which the contact electrode is located.

A styler unit is especially suitable for anchoring a contact electrode in the heart's atrium, so a suitable J-shape can be imparted to the distal end section of the electrode cable, thereby facilitating introduction of the end section into the atrial auricle and anchoring the contact electrode in the trabeculae of the atrial auricle. After the contact electrode has been anchored at the desired site in the heart, the stylet unit is completely removed from the electrode cable, which is then connected to the heart stimulator (e.g. a pacemaker) which is surgically implanted subcutaneously into the body, e.g. under the left pectoral muscle.

U.S. Pat. No. 5,170,787 describes and shows (see FIG. 2 in the document) a double stylet unit (referred to as a "double stylet wire"), i.e. a double stylet combination formed by a flexible, tubular stylet shell containing a movable, internal stylet in the shell's central channel. At the proximal end of this known stylet unit, there is a maneuvering handle with which the shell and the internal stylet can be moved in relation to each other for retracting the stylet's pre-curved distal end section into the surrounding shell's distal end section, or for deploying the pre-curved distal end section of the stylet outside the opening of the shell's end section into the central channel of the distal end section of the surrounding electrode cable, in order to give the distal end section the desired curved shape.

U.S. Pat. No. 4,136,703 shows another example of a stylet unit, devised as a double stylet combination, for an electrode cable. The stylet unit contains a pre-curved internal stylet in its distal end section. The stylet unit is inserted into a hollow, rather "limp" electrode cable in order to produce the required stiffening of the cable during the cable's introduction into the human body and, at the end of this introduction, to achieve bending of the cable's distal end section equipped with a contact electrode. This cable bending is achieved when the pre-curved end section of the internal stylet of the stylet unit is switched from an inactive retracted position inside the shell to an exposed active position outside the opening of the shell. When the stylet's pre-curved end section inside the surrounding cable is exposed, the electrode cable is curved or bent to assume a desired J-shape.

The types of known stylet units described in both the aforementioned patents, however, are incapable of insuring that the stylet unit—and accordingly its surrounding electrode cable—attains a desired, substantially straight configuration when the internal stylet's pre-curved distal end section is retracted into its inactive, "standby" position inside the shell's corresponding distal end section.

U.S. Pat. No. 5,190,546 further describes medical applications (procedures and devices) involving the use of various components made of memory metals. This patent discloses the use of components made of stress-induced martensite alloy, which reduces the thermal sensitivity of the component, thereby facilitating its introduction into or removal from the body of a living subject.

The procedures and devices set forth in the patent claims in the last patent document consistently involve attachment to or anchoring in bone in a body. The disclosed technique aims at preventing the memory metal from undergoing an undesirable martensitic phase shift because the memory metals critical temperature is in about the same temperature range as bone/bony tissue in a living body.

SUMMARY OF THE INVENTION

An object of the present invention is to achieve a new type of stylet unit with which it is possible to attain a much straighter, i.e. with less lateral bending, and much better shape for the distal end section of the stylet shell in a stylet unit devised as a double stylet combination when all of the pre-curved distal end section of the movable internal stylet has been retracted inside the shell's channel and is surrounded by the stylet shell's enclosing distal end section.

The above object is achieved in accordance with the principles of the present invention in a stylet unit introducible into a flexible component, such as a hollow electrode cable, in order to stiffen the flexible component and to bend a distal end section thereof, wherein the stylet unit is a double stylet combination having a flexible, tubular stylet shell with an internal stylet movable therein, and wherein the stylet has a pre-curved distal end section movable, by moving the stylet, between a retracted internal position inside the stylet shell and an exposed, external position projecting beyond the stylet shell, and wherein the pre-curved distal end section of the stylet is made at least in part of memory metal and includes a section having a radius of curvature which varies along a longitudinal axis of the stylet.

When the stylet's pre-curved distal end section has been exposed and deployed outside the opening of the stylet shell, it produces the desired bending of a corresponding section of the narrow, channel equipped flexible component, which holds and surrounds the stylet unit. This component could e.g. be (as noted above) a hollow cable, a catheter or some other kind of hollow, elongate instrument with relatively poor stiffness.

Since the stylet unit according to the invention is designed to stiffen a narrow, flexible component (into which the stylet unit is inserted) and bend a distal end section of this component, an object of the invention is thus also to provide a stylet unit for maneuvering a distal end section of a narrow, flexible component with an internal channel. When the component is a hollow electrode cable, intended for a heart stimulator or pacemaker, an object of the invention is also to provide a stylet unit with which it is possible to manipulate the distal end section of the electrode cable during implantation in the desired manner, i.e. from a virtually straight shape to a curved shape, the end section then being J-shaped.

As the aforementioned documents which elucidate the prior art as regards stylet units show, a typical stylet unit is made of thin-walled tubing with a pre-shaped stylet running inside the tube. When the stylet is moved in relation to the tube (with some kind of control mechanism), its exposed, pre-curved end section outside the end of the tube can be used to impart different shapes to surrounding electrode cable. The internal stylet in this known, typical stylet unit is usually made of stainless steel with a linear relationship between elongation and tension up to a maximum elongation of e.g. 3%. When the internal stylet's pre-curved, distal end section is retracted into the tubular stylet shell, the distal end section acquires a lateral bulge because of the bending moment which the successively retracted pre-curved end section exerts on the shell as the stylet is forced to straighten during retraction into the tubular shell.

As the above shows, however, keeping the stylet unit reasonably straight, even when the internal stylet's pre-curved distal end section has been fully retracted into the stylet shell, is very desirable. In practice, however, this desirable result cannot be achieved with the use of a conventional internal stylet made of stainless steel, since straightening the internal stylet's pre-curved distal end section generates heavy flexural stress in the internal stylet, even when the magnitude of stretching is only 2–3% as is attained even when the "straightening" of the internal stylet's pre-curved end section is limited. The flexural stress generated in the internal stylet when it is forced to straighten imposes internal flexural stress, generated by the stylet, on the surrounding tubular stylet shell.

Thus an internal stylet made of stainless steel is not suitable in this context, since it subjects the surrounding tubular stylet shell to a bending moment so large that bulging of the stylet shell's end section cannot be avoided, even when the stylet only straightens to a modest degree. Another object of the present invention is therefore to select a material, other than stainless steel, which does not lead to inappropriately large flexural stress in the internal stylet, even when the stylet is exposed to maximum stretching exceeding the 3% value cited above for stainless steel.

An additional object of the invention is (as suggested above) to achieve a stylet unit whose internal stylet is able to bend a surrounding, hollow electrode cable enough for the distal end of the cable to assume a pronounced J-shape or fish hook shape all of the pre-curved distal end section of the stylet unit's internal stylet has been deployed outside the opening of the stylet shell. In order to achieve such a pronounced J-shape for the end section of such a hollow electrode cable, into which the stylet unit according to the invention has been inserted, a stylet unit is required which is devised so the internal stylet is able to exert the largest possible bending moment on the surrounding stylet shell—and accordingly on surrounding electrode cable—even in the area in which bending of the stylet shell and the electrode cable's J-shaped bending begin.

A distinctive feature of the stylet unit according to the invention is that the internal stylet's pre-curved distal end section is made at least in part of memory metal and forms a stylet section whose radius of curvature varies longitudinally.

All of the internal stylet's pre-curved distal end section can be suitably made from memory metal. From the fabrication point of view, it may be desirable for the stylet to be made entirely from memory metal, not just its pre-curved distal end section.

For the internal stylet with its pre-curved distal end section to subject the tubular, surrounding stylet shell to a maximum bending moment immediately from the start of the radius of curvature, the stylet's pre-curved distal end section is preferably pre-curved with a radius of curvature whose magnitude increases longitudinally along the stylet section toward its free end. This means that the internal stylet's pre-curved distal end section must have its maximum curvature (i.e., its smallest radius of curvature) at the start of the pre-curved end section and then display decreasing curvature (i.e. an increasing radius of curvature) toward the stylet section's free end.

When the stylet's pre-curved distal end section is partially or wholly made of memory metal, far more efficient use of material is possible than is possible with conventional stainless steel, since memory metal enables the stylet's pre-curved distal end section to withstand maximum stretching up to, e.g., 8%, when this end is retracted into the stylet shell, without the flexural stress caused by the stylet's straightening reaching values so high that the surrounding shell is forced to bulge laterally when the internal stylet's pre-curved end section is fully retracted into the stylet shell and, accordingly, is fully straightened.

The use of memory metal in the stylet's pre-curved distal end section therefore makes it possible to use stylet material more efficiently than is the case when conventional stainless steel is employed. A memory metal is selected which displays pseudoelasticity in the temperature range anticipated for the stylet unit. The fact that the memory metal displays pseudoelasticity means that the metal can be deformed very considerably without any residual deformation after load relief.

An internal stylet made of memory metal therefore achieves the desired result that the internal stylet with its pre-curved distal end section acts on the surrounding stylet shell with a considerably lower bending moment when the stylet has been completely retracted into the shell than would be the case with the use of an internal stylet made of stainless steel.

When memory metal is used in the internal stylet's pre-curved distal end section, however, it must be remembered that this type of material has a much poorer ability to store energy than stainless steel. This shortcoming can be overcome according to the invention when the internal stylet's pre-curved distal end section is devised so it exerts, when "straightened out", a bending moment on the stylet shell which is an appropriate function of the stylet's radius of curvature. This is achieved when the section of the stylet's pre-curved distal end section made of memory metal has a radius of curvature which varies longitudinally in the stylet. This is preferably attained when the memory metal stylet section is pre-curved with a radius of curvature whose magnitude increases longitudinally in the end section toward the section's free end. One such radius of curvature is obtained, e.g., when the stylet's pre-curved distal end section has a spiral shape, such as a hyperbolic or logarithmic spiral.

A suitable memory metal for use in the invention is a nickel-titanium alloy, such as "Nitinol", which displays pseudoelasticity, at least in the 15°–45° C. temperature range.

As examples of the dimensions of the internal stylet and the attendant stylet shell (in a stylet unit f or an electrode cable), a stylet diameter of about 0.20–0.25 mm may be appropriate when the diameter of the shell is 0.30–0.45 mm.

In order to insure relative movement between the internal stylet and the surrounding shell can be achieved without problems, with appropriate friction resistance, the gap, or tolerance, between these interacting components should appropriately amount to at least 0.02 mm.

DESCRIPTION OF THE DRAWINGS

FIG. 1 schematically shows the parts of a known stylet unit in which the internal stylet's pre-curved distal end section is deployed outside the opening of the stylet shell.

FIG. 2 shows the stylet unit depicted in FIG. 1 when the stylet's pre-curved distal end section is completely retracted into and surrounded by the tubular stylet shell's distal end section.

FIG. 3 shows stress-strain curves for stainless steel and memory metal respectively.

DESCRIPTION OF THE PREFERRED EMBODIMENTS

Figure 4:
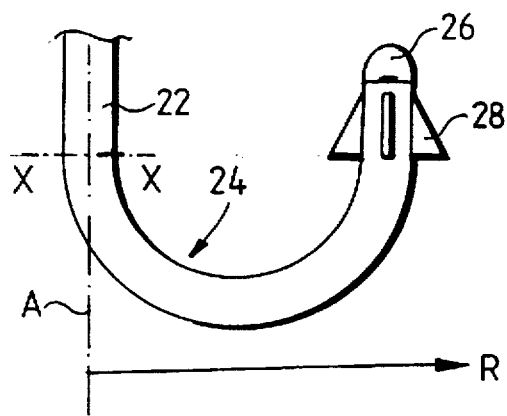
FIG. 4 shows the curved, distal end section of an electrode cable bent by a stylet.

FIGS. 1 and 2 schematically depict a distal end area of a known stylet unit 2, consisting of a double stylet design with a flexible, tubular stylet shell 4 and an internal stylet 6 which is movable inside the channel of the shell 4. The distal end of the stylet shell 14 is designated 8, the proximal end of the shell 14 is designated 10 and the proximal end of the stylet is designated 12. As shown in FIG. 1, the internal stylet 6 has a pre-curved distal end section 14 which, in the depicted example, is primarily a semicircular section with a radius of curvature $D_1$ and a short, straight stylet end section 16 with a stop ball 18 to prevent the end section 14 from being unintentionally retracted too far into the stylet shell 4 and to minimize the risk of the stylet end section 16 penetrating the wall of a surrounding electrode lead (not shown).

When the stylet unit 2 has been completely retracted into such a longitudinally hollow electrode cable (not shown), the pre-curved distal end section 14 in its exposed position induces the electrode cable's distal end section to assume a J-shape, as shown in FIG. 4.

FIG. 2 shows a section of the stylet unit 2 when the pre-curved distal end section 14 of the internal stylet 6 has been fully retracted into the end section of the stylet shell 4, causing the stop ball 18 to press against the distal end 8 of the opening at the tubular stylet shell 4. When the stylet's distal end section 14 has the semicircular shape shown in FIG. 1, there is attendant lateral bulging or bending of the end section of the stylet shell 4—after the entire length of the stylet end section 14 has been retracted into and is enclosed in the stylet shell 4. This causes the shell end 8 to have a laterally projecting position corresponding to a lateral deviation L from the longitudinal axis A of the straight tubular stylet shell 4, shown to the left in FIGS. 1 and 2.

Known stylet units of the type shown in FIGS. 1 and 2 are made of metal, i.e., stainless steel, whose stress-strain curve 20 is shown in FIG. 3. In the diagram in FIG. 3 the horizontal g axis designates the respective material's elongation expressed s as a percent, whereas the vertical axis δ designates the materials stress, e.g., expressed in Mpa.

When the pre-curved distal end section 14 of the stylet 6 is retracted into the stylet shell 4, the stylet shell causes the end section 14 to partially straighten, since the shell 4 is more resistant to bending than the stylet section 14. The shell 4, however, is unable to straighten the stylet section 14 completely, while retaining the entirely straight shape shown in FIG. 1, and the shell 4 itself acquires the bulge shown in FIG. 2. This bulging is caused by the bending moment exerted by the partially straightened stylet end section 14 on the surrounding part of the stylet shell 4. The lateral bulging of the end section of the stylet shell 4 shown in FIG. 2 causes an increase in the flexural stress in the material in the tubular stylet shell 4. The curve 20 in FIG. 3 illustrates the relationship between stress and strain for stainless steel of the kind used both for the internal stylet 6 and the surrounding stylet shell 4 in a known stylet unit of the kind shown in FIGS. 1 and 2. Flexural loading according to FIG. 2 thus generates considerable flexural stress in the stylet shell 4, even when elongation only amounts to about 3%.

When the stylet unit 2 has been inserted into a hollow electrode cable 22 of the kind schematically depicted in FIG. 4 and when the stylet shell 4 and internal stylet 6 have been set to the position shown in FIG. 1, the hollow electrode cable 22 will have a curved distal end section 24 with the approximate shape shown in FIG. 4. In FIG. 4 an electrode contact head on the free end of the cable 22 has been designated 26 and four adjacent fins are designated 28.

If elementary beam bending theory is considered, it will be readily understood the cable is subjected to its maximum bending moment at about the section line X—X in FIG. 4 in order for the end section 24 of the cable 22 to assume the curved shape shown in FIG. 4. This means that the exposed, pre-curved distal end section 14 of the stylet unit 2 inserted into the cable 22 must exert its maximum bending moment on the surrounding electrode cable 22 at the beginning of its pre-curved distal end section 24, about at the section line X—X in FIG. 1.

The aim for an internal stylet, whose pre-curved section 14 (in the position shown in FIG. 1) is intended to induce the electrode cable 22 to achieve a maximum bending moment at the section line X—X and (in the position shown in FIG. 2), is to achieve without subjecting the surrounding stylet shell 4 to a bending moment so great that the shell bulges into a shape like the one shown in FIG. 2. Instead it is desirable for the internal stylet 6, in the position shown in FIG. 2, to be largely incapable of bending the surrounding stylet shell 4, which should remain virtually straight even when the internal stylet 6 is fully retracted. These two desirable properties for the internal stylet 6, however, are competing and cannot be successfully realized with a conventional stylet unit using a stylet made of stainless steel.

In order to achieve both of these desirable properties for the internal stylet, the present invention has recognized that the steel must be replaced with a material which is capable of withstanding much greater flexural stress and, accordingly, elongation (without being a plastic). It must also simultaneously generate much lower flexural stress when elongation is much greater.

These problems can be effectively solved with a stylet unit according to the invention in which the stylet's pre-curved distal end section is made wholly or partially of memory metal while providing the end section with a varying radius of curvature.

Figure 5:
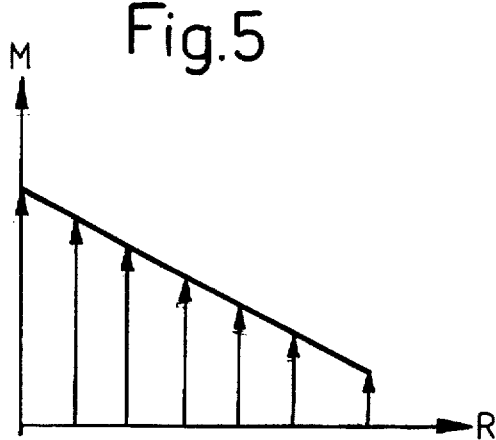
FIG. 5 shows the distribution of bending moment for the curved electrode cable section shown in FIG. 4.

FIG. 3 shows with bold contours the stress-strain characteristics for an appropriate memory metal in this context. The curve 30 illustrates the g-F relationship when the load successively increases, whereas the curve 32 shows the corresponding relationships when the load is successively reduced. FIG. 3 clearly shows that fabricating the internal stylet from an appropriate memory metal makes it possible to utilize the stylet material much better than when steel is used, since much greater elongation (e.g. 8%) is possible without strain approaching the strain achieved with steel when elongation only amounts to 3%. A major advantage of an internal stylet made of memory metal is that the stylet will act on the surrounding stylet shell with a much lower bending moment (than if the stylet were made of stainless steel) when the stylet has been retracted back into the shell, corresponding to the situation depicted in FIG. 2. In order to simultaneously achieve both an internal stylet which is capable of exerting the bending moment illustrated in FIGS. 4 and 5 on a surrounding electrode cable, the stylet's pre-curved distal end section must simultaneously be devised to be able to store the energy needed to produce the desired curvature of the electrode cable. According to the invention, this is achieved when the stylet's pre-curved distal end section has at least one stylet section whose radius of curvature varies along the section's longitudinal direction.

Figure 6:
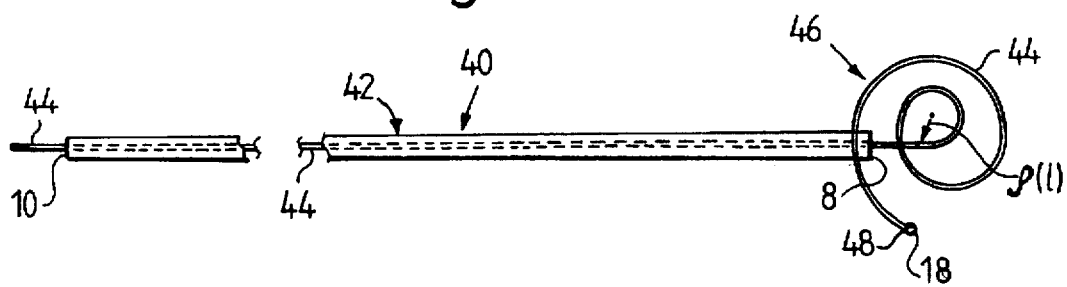
FIG. 6 schematically depicts a stylet unit according to the invention when the internal stylet's pre-curved distal end section is completely outside the stylet shell's opening.

FIG. 6 shows an example of a stylet unit 40 according to the invention. This stylet unit 40 has a flexible, tubular stylet shell 42 and a movable internal stylet 44, inside the shell's channel, with a pre-curved distal end section 46 made of a memory metal and having a radius of curvature P(l) which increases as a function of the longitudinal length l of the distal end section 46 toward the free end 48 of the stylet end section 46.

The pre-curved distal stylet section 46 is shown in FIG. 6 in the form of a spiral-shaped, pre-curved distal end section.

With a stylet unit 40 according to the invention, the bending moment M exerted by the pre-curved distal end section 46 of the internal stylet 44 on the end section 24 of a surrounding electrode cable 22 will be a function of the stylet's radius of curvature P(l), i.e. M=f[P(l)]. In this manner, the internal stylet 44 is able to bend, using its exposed, pre-curved end section 46, the surrounding electrode cable 22 into the J-shape shown in FIG. 4 without acting on the stylet shell 42 (in its retracted position corresponding to the situation depicted in FIG. 2) as strongly as would have been the case with a conventional stylet unit using an internal stylet made of stainless steel.

Finally, it should be noted that the projection of the pre-curved end section 46 from, and retraction into, the stylet shell 42 is achieved in practice with a manipulation and holding device (not shown) arranged at the proximal end 10 of the shell 42. In practice, retraction of the pre-curved end section 46 of the internal stylet 44 into the stylet shell 42 is appropriately achieved when the shell 42 is moved in relation to the stylet 44 toward the free end 48 of the stylet section 46.

Although modifications and changes may be suggested by those skilled in the art, it is the intention of the inventor to embody within the patent warranted hereon all changes and modifications as reasonably and properly come within the scope of his contribution to the art.

I claim as my invention:

1. A stylet unit introducible into a flexible, hollow component for temporarily stiffening the flexible component and for bending a distal end section of the flexible component, said stylet unit comprising:

a flexible, tubular straight stylet shell having an internal longitudinal channel; and an internal stylet movably disposed inside said channel, said internal stylet having a longitudinal axis and having a pre-curved distal end section movable between a retracted position completely inside said stylet shell without causing bending of said stylet shell and a deployed position projecting beyond said stylet shell and forming a J-shape, said pre-curved distal end section being at least partially composed of memory metal and including a stylet section having a radius of curvature which varies along said longitudinal axis of said stylet.

2. A stylet unit as claimed in claim 1 wherein said pre-curved distal end section terminates in a free end, wherein said pre-curved distal end section is composed entirely of memory metal, and wherein said radius of curvature of said stylet section increases from a smallest radius at a beginning of said stylet section farthest from said free end to a largest radius of curvature at an end of said stylet section closest to said free end.

3. A stylet unit as claimed in claim 1 wherein said internal stylet is composed of memory metal.

4. A stylet unit as claimed in claim 2 wherein said pre-curved distal end section of said internal stylet has a shape approximating a spiral.

5. A stylet unit as claimed in claim 4 wherein said pre-curved distal end section of said internal stylet has a shape approximating a hyperbolic spiral.

6. A stylet unit as claimed in claim 4 wherein said pre-curved distal end section of said internal stylet has a shape approximating a logarithmic spiral.

7. A stylet unit as claimed in claim 1 wherein said memory metal comprises a nickel-titanium alloy display pseudoelasticity at least in a temperature range between 15° C. and 45° C.

* * * * *